(12) United States Patent
Didier et al.

(10) Patent No.: US 9,309,210 B2
(45) Date of Patent: Apr. 12, 2016

(54) CRYSTALLINE FORM OF CABAZITAXEL AND PROCESS FOR PREPARING THE SAME

(71) Applicant: Aventis Pharma SA, Antony (FR)

(72) Inventors: Eric Didier, Paris (FR); Nicolas Tremaudeux, Paris (FR); Lionel Zaske, Saint Maurice (FR)

(73) Assignee: AVENTIS PHARMA S.A., Antony (FR)

( * ) Notice: Subject to any disclaimer, the term of this patent is extended or adjusted under 35 U.S.C. 154(b) by 0 days.

(21) Appl. No.: 14/301,740

(22) Filed: Jun. 11, 2014

(65) Prior Publication Data

US 2014/0343133 A1   Nov. 20, 2014

Related U.S. Application Data

(63) Continuation of application No. PCT/IB2012/057170, filed on Dec. 11, 2012.

(30) Foreign Application Priority Data

Dec. 13, 2011 (EP) ..................................... 11306644

(51) Int. Cl.
*C07D 305/14* (2006.01)
(52) U.S. Cl.
CPC .................................. *C07D 305/14* (2013.01)
(58) Field of Classification Search
CPC .................................................. C07D 305/14
USPC ........................................................ 549/510
See application file for complete search history.

(56) References Cited

U.S. PATENT DOCUMENTS

| 5,847,170 | A | 12/1998 | Bouchard et al. |
| 6,346,543 | B1 | 2/2002 | Bissery et al. |
| 7,241,907 | B2 | 7/2007 | Didier et al. |
| 8,378,128 | B2 | 2/2013 | Billot et al. |
| 8,575,373 | B2 | 11/2013 | Henschke et al. |
| 8,735,611 | B2 | 5/2014 | Henschke et al. |
| 8,901,322 | B2 * | 12/2014 | Lahiri et al. ................. 549/351 |
| 2013/0065955 | A1 | 3/2013 | Henschke et al. |
| 2013/0178639 | A1 | 7/2013 | Billot et al. |
| 2013/0211109 | A1 | 8/2013 | Lahiri et al. |

FOREIGN PATENT DOCUMENTS

| WO | WO 96/30355 | 10/1996 |
| WO | WO 2005/028462 | 3/2005 |
| WO | WO 2009/115655 | 9/2009 |
| WO | WO 2011/051894 | 5/2011 |
| WO | WO 2013/080217 | 6/2013 |

OTHER PUBLICATIONS

U.S. Appl. No. 61/533,111, filed Sep. 9, 2011, Henschke, et al.
International Search Report for WO2013/088335 dated Jun. 20, 2013.
Caira, Crystalline Polymorphism of Organic Compounds, Topics in Current Chemistry, (1998), pp. 163-208, vol. 198.
Bryn, et al., Solid-Slate Chemistry of Drugs, 2nd edition, (1999), SSCI, Inc., pp. 232-247.
Chawla, et al., Challenges in Polymorphism of Pharmaceuticals, CRIPS, vol. 5, No. 1, (Jan.-Mar. 2004), pp. 9-12.
Rodriguez-Spong, et al., General principles of pharmaceutical solid polymorphism: a supramolecular perspective, Advanced Drug Delivery Reviews, vol. 56, (2004), pp. 241-274.
Souillac, et al., Characterization of Delivery Systems, Differential Scanning Calorimetry, Encyclopedia of Controlled Drug Delivery, (1999), John Wiley & Sons, pp. 212-227.

\* cited by examiner

*Primary Examiner* — Andrew D Kosar
*Assistant Examiner* — Raymond Covington
(74) *Attorney, Agent, or Firm* — Kelly L. Bender

(57) ABSTRACT

The present invention relates to a novel crystalline ethyl acetate solvate form of cabazitaxel or 4α-acetoxy-2α-benzoyloxy-5β,20-epoxy-1β-hydroxy-7β,10β-dimethoxy-9-oxo-11-taxen-13α-yl(2R,3S)-3-tert-butoxycarbonylamino-2-hydroxy-3-phenylpropionate and process for preparing the same.

1 Claim, 1 Drawing Sheet

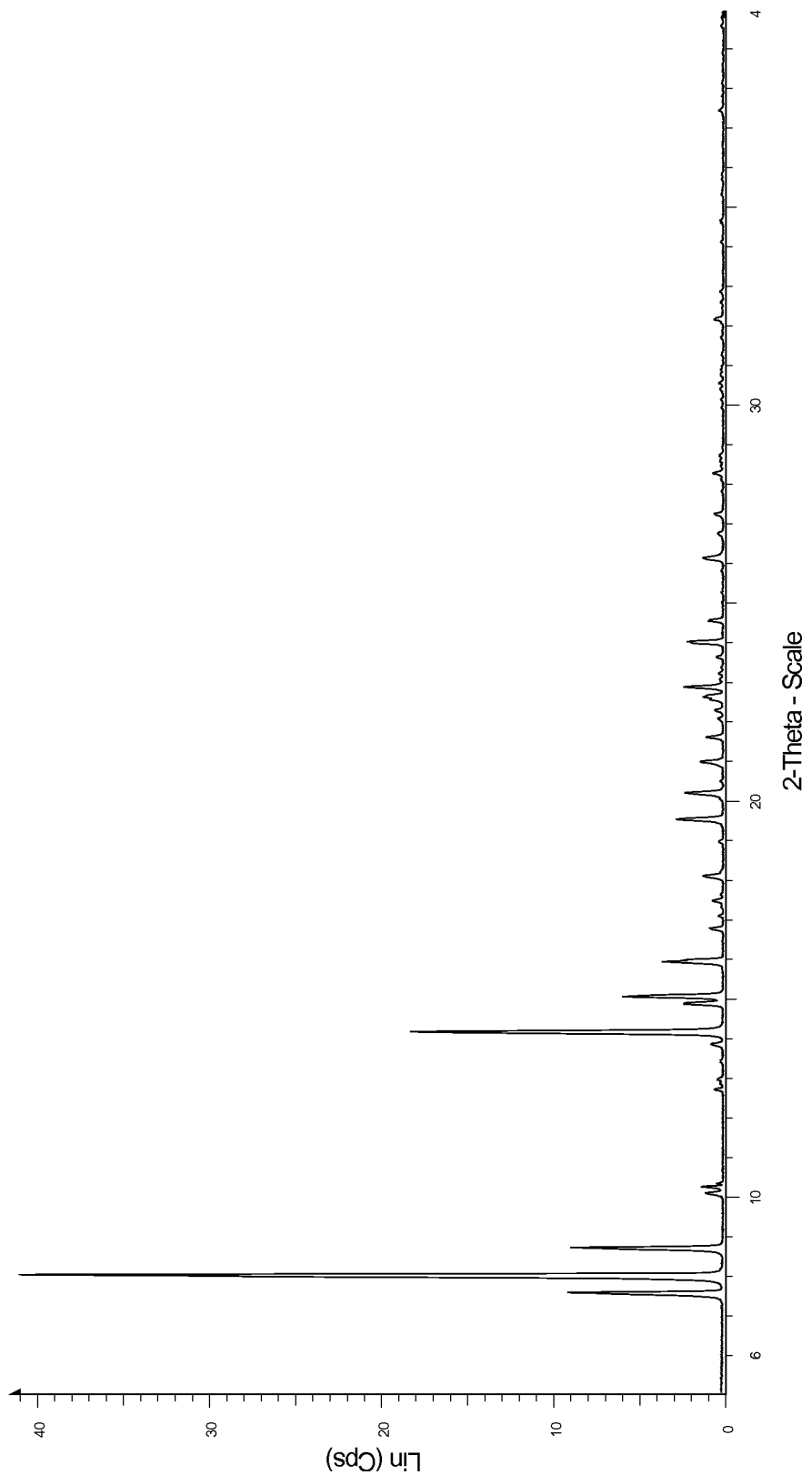

CRYSTALLINE FORM OF CABAZITAXEL AND PROCESS FOR PREPARING THE SAME

This application is a continuation of International Application No. PCT/IB2012/057170, filed Dec. 11, 2012, which is incorporated herein by reference, and which claims priority to European Application No. 11306644.3, filed Dec. 13, 2011.

The present invention relates to a novel crystalline form of cabazitaxel or 4'-acetoxy-2α-benzoyloxy-5β,20-epoxy-1β-hydroxy-7β,10β-dimethoxy-9-oxo-11-taxen-13α-yl(2R,3S)-3-tert-butoxycarbonylamino-2-hydroxy-3-phenylpropionate.

The invention also relates to the process for the preparation of said novel crystalline form, pharmaceutical compositions and medicament comprising it, and its therapeutic use in the prevention and/or treatment of cancers, more particularly prostate cancer.

The 4α-acetoxy-2α-benzoyloxy-5β,20-epoxy-1β-hydroxy-7β,10β-dimethoxy-9-oxo-11-taxen-13α-yl(2R,3S)-3-tert-butoxycarbonylamino-2-hydroxy-3-phenylpropionate, which has the following structure of formula (I):

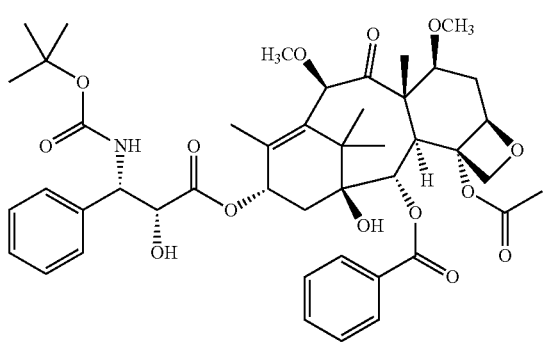

exhibits notable anticancer properties and is particularly interesting for preventing and/or treating prostate cancers. Prostate cancer affects a large proportion of the male population worldwide, it is the most frequently occurring cancer in men after lung cancer.

The use of 4α-acetoxy-2α-benzoyloxy-5β,20-epoxy-1β-hydroxy-7β,10β-dimethoxy-9-oxo-11-taxen-13α-yl(2R,3S)-3-tert-butoxycarbonylamino-2-hydroxy-3-phenylpropionate in the treatment of prostate cancer is known and described in WO 2011/051894.

The process for the preparation of 4α-acetoxy-2α-benzoyloxy-5β,20-epoxy-1β-hydroxy-7β,10β-dimethoxy-9-oxo-11-taxen-13α-yl(2R,3S)-3-tert-butoxycarbonylamino-2-hydroxy-3-phenylpropionate is described more particularly in WO 96/30355.

Finally, crystalline acetone solvate form of 4α-acetoxy-2α-benzoyloxy-5β,20-epoxy-1β-hydroxy-7β,10β-dimethoxy-9-oxo-11-taxen-13α-yl(2R,3S)-3-tert-butoxycarbonylamino-2-hydroxy-3-phenylpropionate is known and described in WO 2005/028462.

Crystalline ethanol solvates, anhydrous and hydrated forms of this compound are also known and described in WO 2009/115655.

The present invention is concerned with the obtaining of a new active crystalline form of such a compound.

Indeed, it is known that the identification of new crystalline forms of active principle useful for preventing and/or treating cancers may be particularly interesting.

It is also known that the ability of a substance to exist in more than one crystal form is defined as polymorphism and its different crystal forms are called polymorphs.

In general, polymorphism is due to the ability of a compound to change its molecular conformation or to form different inter- and/or intra-molecular interactions, particularly hydrogen bonds, which is reflected in different atom arrangements in the crystal lattice of different polymorphs. Thus, polymorphs of a compound can differ notably from each other by different energies in their crystal lattices and, therefore, generally have specific physical properties in the solid state such as crystal morphology, density, melting point, colour, chemical and physical stability, hygroscopy, solubility, dissolution rate, granular properties.

In other words, polymorphic forms of the same compound can exhibit different behaviors in terms of formulation, therapeutic activity and chemical and physical stability.

Unexpectedly, the inventors have discovered that the 4α-acetoxy-2α-benzoyloxy-5β,20-epoxy-1β-hydroxy-7β,10β-dimethoxy-9-oxo-11-taxen-13α-yl(2R,3S)-3-tert-butoxycarbonylamino-2-hydroxy-3-phenylpropionate can exist in a crystalline ethyl acetate solvate form.

Thus, the present invention provides a novel crystalline ethyl acetate solvate form of the 4α-acetoxy-2α-benzoyloxy-5β,20-epoxy-1β-hydroxy-7β,10β-dimethoxy-9-oxo-11-taxen-13α-yl(2R,3S)-3-tert-butoxycarbonylamino-2-hydroxy-3-phenylpropionate.

Advantageously, this novel crystalline ethyl acetate solvate form of the cabazitaxel is obtained in higher purity than the acetone solvate form, as illustrated in the examples.

Further, this new crystalline ethyl acetate solvate form of the cabazitaxel may be stored for a long time without the need for specific conditions to prevent a premature vaporization of the solvent ethyl acetate contrary to the prior crystalline forms having solvent like acetone or ethanol.

This slower desolvatation over time compared to the crystalline ethanol solvate form and crystalline acetone solvate form is also an advantage for the handling.

In particular, the crystalline ethyl acetate solvate form has the following characteristics: X-Ray Powder Diffraction (XRPD) pattern having the peaks at 8.7, 10.1, 13.8, 14.1 and 14.8±0.2 degrees 2-theta.

More particularly, said crystalline ethyl acetate solvate form has the following characteristics: X-Ray Powder Diffraction (XRPD) pattern having the peaks at 7.5, 7.9, 8.7, 10.1, 10.2, 12.6, 12.9, 13.8, 14.1 and 14.8±0.2 degrees 2-theta.

More particularly, the novel crystalline ethyl acetate solvate form of the 4α-acetoxy-2α-benzoyloxy-5β,20-epoxy-1β-hydroxy-7β,10β-dimethoxy-9-oxo-11-taxen-13α-yl(2R,3S)-3-tert-butoxycarbonylamino-2-hydroxy-3-phenylpropionate having the above defined characteristics, is defined as form A.

Another aspect of the present invention is the process for the preparation of said crystalline ethyl acetate solvate form of 4α-acetoxy-2α-benzoyloxy-5β,20-epoxy-1β-hydroxy-7β,10β-dimethoxy-9-oxo-11-taxen-13α-yl(2R,3S)-3-tert-butoxycarbonylamino-2-hydroxy-3-phenylpropionate.

Thus, the present invention is directed to a particular process for preparing said crystalline ethyl acetate solvate form of 4α-acetoxy-2α-benzoyloxy-5β,20-epoxy-1β-hydroxy-7β,10β-dimethoxy-9-oxo-11-taxen-13α-yl(2R,3S)-3-tert-butoxycarbonylamino-2-hydroxy-3-phenylpropionate, said process comprising at least the following steps:

having the 4α-acetoxy-2α-benzoyloxy-5β,20-epoxy-1β-hydroxy-7β,10β-dimethoxy-9-oxo-11-taxen-13α-yl(2R,3S)-3-tert-butoxycarbonylamino-2-hydroxy-3- phenylpropionate in solution in an organic solvent (for example acetone or methylene chloride) at room temperature;

making a change of solvent to ethyl acetate at atmospheric or under reduced pressure;

maintaining the so-formed solution in ethyl acetate on continued stirring, and recovering said crystalline ethyl acetate solvate form of 4α-acetoxy-2α-benzoyloxy-5β,20-epoxy-1β-hydroxy-7β,10β-dimethoxy-9-oxo-11-taxen-13α-yl(2R,3S)-3-tert-butoxycarbonylamino-2-hydroxy-3-phenylpropionate.

Said process is particularly advantageous over those disclosed in the prior art since it provides a crystalline ethyl acetate solvate form of 4α-acetoxy-2α-benzoyloxy-5β,20-epoxy-1β-hydroxy-7β,10β-dimethoxy-9-oxo-11-taxen-13α-yl(2R,3S)-3-tert-butoxy carbonylamino-2-hydroxy-3-phenylpropionate in good yields and with good chemical purity.

The present invention also relates to said crystalline ethyl acetate solvate form of 4α-acetoxy-2α-benzoyloxy-5β,20-epoxy-1β-hydroxy-7β,10β-dimethoxy-9-oxo-11-taxen-13α-yl(2R,3S)-3-tert-butoxycarbonylamino-2-hydroxy-3-phenylpropionate as a medicament.

In a further aspect, the present invention provides said crystalline ethyl acetate solvate form of 4α-acetoxy-2α-benzoyloxy-5β,20-epoxy-1β-hydroxy-7β,10β-dimethoxy-9-oxo-11-taxen-13α-yl(2R,3S)-3-tert-butoxycarbonylamino-2-hydroxy-3-phenylpropionate for its use for preventing and/or treating cancers.

Crystalline Ethyl Acetate Solvate Form of Cabazitaxel

In a preferred aspect, the invention provides a crystalline ethyl acetate solvate form of 4α-acetoxy-2α-benzoyloxy-5β, 20-epoxy-1β-hydroxy-7β,10β-dimethoxy-9-oxo-11-taxen-13α-yl(2R,3S)-3-tert-butoxycarbonylamino-2-hydroxy-3-phenylpropionate as herein defined substantially free of impurities.

By "substantially free", it is meant that the crystalline ethyl acetate solvate form comprises less than 2% of impurities, preferably less than 1.5% of impurities, and more preferably less than 0.9% of impurities.

In a another preferred embodiment, said crystalline ethyl acetate solvate form of 4α-acetoxy-2α-benzoyloxy-5β,20-epoxy-1β-hydroxy-7β,10β-dimethoxy-9-oxo-11-taxen-13α-yl(2R,3S)-3-tert-butoxycarbonylamino-2-hydroxy-3-phenylpropionate, has a X-Ray Powder Diffraction (XRPD) diagram exhibiting characteristic lines located at 8.7, 10.1, 13.8, 14.1 and 14.8±0.2 degrees 2-theta.

More particularly said crystalline ethyl acetate solvate form of 4α-acetoxy-2α-benzoyloxy-5β,20-epoxy-1β-hydroxy-7β,10β-dimethoxy-9-oxo-11-taxen-13α-yl(2R,3S)-3-tert-butoxycarbonylamino-2-hydroxy-3-phenylpropionate, has a X-Ray Powder Diffraction (XRPD) diagram exhibiting characteristic lines located at 7.5, 7.9, 8.7, 10.1, 10.2, 12.6, 12.9, 13.8, 14.1 and 14.8±0.2 degrees 2-theta (see FIG. 1).

More particularly the novel crystalline ethyl acetate solvate form of the 4α-acetoxy-2α-benzoyloxy-5β,20-epoxy-1β-hydroxy-7β,10β-dimethoxy-9-oxo-11-taxen-13α-yl(2R,3S)-3-tert-butoxycarbonylamino-2-hydroxy-3-phenylpropionate having the above defined characteristics is defined as form A.±0.2 degrees 2-theta.

The ethyl acetate content was determined by Gas Chromatography (GC). The obtained value is of about 9.5% m/m, an ethyl acetate mole per cabazitaxel mole.

Process for Preparing Crystalline Ethyl Acetate Solvate Form of Cabazitaxel

As stated previously, another aspect of the present invention is the process for the preparation of the crystalline ethyl acetate solvate form of 4α-acetoxy-2α-benzoyloxy-5β,20-epoxy-1β-hydroxy-7β,10β-dimethoxy-9-oxo-11-taxen-13α-yl(2R,3S)-3-tert-butoxy carbonylamino-2-hydroxy-3-phenylpropionate.

Said process for preparing the crystalline ethyl acetate solvate form may comprise the following steps:

having the 4α-acetoxy-2α-benzoyloxy-5β,20-epoxy-1β-hydroxy-7β,10β-dimethoxy-9-oxo-11-taxen-13α-yl (2R,3S)-3-tert-butoxycarbonylamino-2-hydroxy-3-phenylpropionate in solution in an organic solvent (for example acetone or methylene chloride) at room temperature;

making a change of solvent to ethyl acetate at atmospheric or under reduced pressure;

maintaining the so-formed solution in ethyl acetate on continued stirring, and recovering said crystalline ethyl acetate solvate form of 4α-acetoxy-2α-benzoyloxy-5β,20-epoxy-1β-hydroxy-7β,10β-dimethoxy-9-oxo-11-taxen-13α-yl(2R,3S)-3-tert-butoxycarbonylamino-2-hydroxy-3-phenylpropionate.

Regarding the step 1, the solution may be prepared by dissolving crude 4α-acetoxy-2α-benzoyloxy-5β,20-epoxy-1β-hydroxy-7β,10β-dimethoxy-9-oxo-11-taxen-13α-yl(2R, 3S)-3-tert-butoxycarbonylamino-2-hydroxy-3-phenylpropionate in six volumes of acetone at room temperature.

The change of solvent to ethyl acetate can be made under reduced pressure or at atmospheric pressure depending of the boiling point of the solvent used, preferably at constant volume under reduced pressure (for example 80 mbar at about 14° C. with acetone).

To maintain the so-formed solution in ethyl acetate in step 3, the slurry volume can be adjusted to 10 volumes by casting of ethyl acetate.

Finally, regarding the step 4, to obtain the crystalline ethyl acetate solvate form of cabazitaxel, the slurry may be filtered and the resulting cake washed with ethyl acetate. This cake may be dried under vacuum at 38° C. for 15 H.

As states previously, said process is particularly advantageous over those disclosed in the prior art since it provides a crystalline ethyl acetate solvate form of 4α-acetoxy-2α-benzoyloxy-5β,20-epoxy-1β-hydroxy-7β,10β-dimethoxy-9-oxo-11-taxen-13α-yl(2R,3S)-3-tert-butoxy carbonyl amino-2-hydroxy-3-phenylpropionate in good yields and with good chemical purity.

By "good yield" in the present invention, it is meant that said ethyl acetate solvate form is obtained in a yield higher than or equal to 80%.

As used herein a "good chemical purity" is a purity which is higher than or equal to 99%.

Application

The present invention is also directed to a medicament comprising said crystalline ethyl acetate solvate form of 4α-acetoxy-2α-benzoyloxy-5β,20-epoxy-1β-hydroxy-7β, 10β-dimethoxy-9-oxo-11-taxen-13α-yl(2R,3S)-3-tert-butoxy carbonylamino-2-hydroxy-3-phenylpropionate.

Thus, the present invention also relates to a pharmaceutical composition comprises said crystalline ethyl acetate solvate form of 4α-acetoxy-2α-benzoyloxy-5β,20-epoxy-1β-hydroxy-7β,10β-dimethoxy-9-oxo-11-taxen-13α-yl(2R,3S)-3-tert-butoxy carbonylamino-2-hydroxy-3-phenylpropionate and also at least one pharmaceutically acceptable excipient.

All components of the present compositions must be pharmaceutically acceptable.

As used herein, a "pharmaceutically acceptable" component is one that is suitable for use with humans and/or other animals without undue adverse side effects (such as toxicity, irritation and allergic response) commensurate with a reasonable benefit/risk ratio.

The compositions of the present invention are generally administered to patients, which include, but are not limited to, mammals, for example, humans, by conventional routes known in the art.

The present invention further relates to the use of the ethyl acetate solvate crystalline form according to the invention, as a medicament.

The present invention further relates to the use of the ethyl acetate solvate crystalline form according to the invention, as a medicament in the prevention and/or treatment of cancers.

For example, the cancer may be prostate cancer.

BRIEF DESCRIPTION OF THE DRAWING

FIG. 1: XRPD pattern ($\lambda_{Cu}$=1.5406 Å) of ethyl acetate solvate form of cabazitaxel.

The examples that follow describe the preparation of crystalline ethyl acetate solvate form of cabazitaxel and its purity. These examples are not limiting, and serve merely to illustrate the present invention.

EXAMPLE 1

Preparation of Crystalline Ethyl Acetate Solvate Form of Cabazitaxel

The crude 4α-acetoxy-2α-benzoyloxy-5β,20-epoxy-1β-hydroxy-7β,10β-dimethoxy-9-oxo-11-taxen-13α-yl(2R,3S)-3-tert-butoxycarbonylamino-2-hydroxy-3-phenylpropionate has been dissolved in six volumes of acetone, at room temperature.

The change of solvent to ethyl acetate under reduced pressure and at constant volume has been made at 80 mbar and T=14.4° C.

The slurry volume has been adjusted to 10 volumes by casting of ethyl acetate.

After two hours under continued stirring, the slurry has been filtered and the resulting cake washed with ethyl acetate.

Said cake has been dried under vacuum at 38° C. for 15 H.

EXAMPLE 2

Purity of the Ethyl Acetate Solvate Form of Cabazitaxel

Cabazitaxel synthesized by the conventional process (crystallized as acetone solvate in acetone/water, see WO2005/028462) and enriched with impurities has been purified by formation of the ethyl acetate solvate form. Results are compared with the cabazitaxel purified by the conventional process.

The obtained results are summarized in the following table.

| Impurities | Starting cabazitaxel | Purified cabazitaxel with AcOEt crystallization treatment | Purified cabazitaxel with conventional process (crystallized in acetone/water) |
|---|---|---|---|
| Total | 1.52% | 0.71% | 0.98% |
| p-anisaldéhyde | 0.02% | Undetected | Undetected |
| Impurity A | 0.02% | 0.01% | 0.01% |
| Impurity B | 0.16% | 0.14% | 0.10% |
| Impurity C | 0.21% | 0.18% | 0.20% |
| Impurity D | 0.02% | Undetected | Undetected |
| Impurity E | 0.17% | 0.12% | 0.11% |
| Impurities F + G | 0.18% | 0.05% | 0.14% |
| Impurity H | 0.25% | 0.10% | 0.12% |
| Impurity I | 0.34% | 0.12% | 0.24% |
| Impurity J | 0.21% | 0.05% | 0.07% |

These results show that ethyl acetate treatment has a higher purifying power.

More particularly, cabazitaxel treated with ethyl acetate has less impurities F+G and I.

Characterizations

Said crystalline ethyl acetate solvate form according to the invention was characterized by X-Ray Powder Diffraction (XRPD) and Gas Chromatography (GC) as shown below.

a) X-Ray Powder Diffraction (XRPD):

Experimental diagram is recorded at ambient conditions on a PANalytical X'Pert Pro MPD powder diffractometer using the Bragg-Brentano (vertical θ-2θ configuration) parafocusing geometry coupled with a X'Celerator detector. A sealed copper anode X-ray tube is used, running at 45 kV and 40 mA levels. An incident beam monochromator (Johansson type: a symmetrically cut curved germanium (111) crystal) produces pure Cu K$\alpha_1$ radiation ($\lambda$=1.54060 Å). A thin layer of the product is deposited on a single-crystal silicon wafer, cut out according to Si (510) crystallographic orientation that, by systematic extinction, impedes any Bragg reflection. In order to bring more crystallites into the diffraction position and thus reduce the influence of particle statistics on the measurements, a sample spinner is used. The spinner rotation speed is set at 1 revolution per second. The angular range extends from 1.5 to 40° in 2θ, with a 0.017° step size in 2θ. A counting time of 500 seconds per step was used.

FIG. 1 shows XRPD pattern obtained for ethyl acetate solvate form of cabazitaxel. Characteristic peaks at 7.5, 7.9, 8.7, 10.1, 10.2, 12.6, 12.9, 13.8, 14.1 and 14.8±0.2 degrees 2-theta are observed in the pattern of crystalline ethyl acetate solvate form of cabazitaxel.

b) Gas Chromatography:

The content of ethyl acetate has been determined by Gas Chromatography (GC) on a Rtx®-200 column (fused silica).

The obtained value is of about 9.5% m/m, an ethyl acetate mole per cabazitaxel mole.

What is claimed is:

1. A process for the preparation of a crystalline ethyl acetate solvate form of 4α-acetoxy-2α-benzoyloxy-5β,20-epoxy-1β-hydroxy-7β,10β-dimethoxy-9-oxo-11-taxen-13α-yl(2R,3S)-3-tert-butoxycarbonylamino-2-hydroxy-3-phenylpropionate comprising the following steps:

having the 4α-acetoxy-2α-benzoyloxy-5β,20-epoxy-1β-hydroxy-7β,10β-dimethoxy-9-oxo-11-taxen-13α-yl (2R,3S)-3-tert-butoxycarbonylamino-2-hydroxy-3-phenylpropionate in solution in an organic solvent at room temperature;

making a change of solvent to ethyl acetate at atmospheric or under reduced pressure;
maintaining the so-formed solution in ethyl acetate on continued stirring, and
recovering said crystalline ethyl acetate solvate form of 4α-acetoxy-2α-benzoyloxy-5β,20-epoxy-1β-hydroxy-7β,10β-dimethoxy-9-oxo-11-taxen-13α-yl(2R,3S)-3-tert-butoxycarbonylamino-2-hydroxy-3-phenylpropionate.

\* \* \* \* \*